(12) United States Patent
Cai et al.

(10) Patent No.: US 9,097,645 B2
(45) Date of Patent: Aug. 4, 2015

(54) METHOD AND SYSTEM FOR HIGH SPEED HEIGHT CONTROL OF A SUBSTRATE SURFACE WITHIN A WAFER INSPECTION SYSTEM

(71) Applicant: KLA-Tencor Corporation, Milpitas, CA (US)

(72) Inventors: Zhongping Cai, Fremont, CA (US); Jingyi Xiong, Sunnyvale, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 14/463,225

(22) Filed: Aug. 19, 2014

(65) Prior Publication Data

US 2015/0055141 A1 Feb. 26, 2015

Related U.S. Application Data

(60) Provisional application No. 61/869,379, filed on Aug. 23, 2013.

(51) Int. Cl.
| | |
|---|---|
| *G01N 21/01* | (2006.01) |
| *G01N 21/13* | (2006.01) |
| *G01N 21/95* | (2006.01) |
| *G01B 11/14* | (2006.01) |

(52) U.S. Cl.
CPC .............. G01N 21/13 (2013.01); G01B 11/14 (2013.01); G01N 21/9501 (2013.01); *G01N 21/01* (2013.01); *G01N 2021/135* (2013.01)

(58) Field of Classification Search
USPC ............................. 356/614–625, 237.1–237.5
See application file for complete search history.

(56) References Cited

U.S. PATENT DOCUMENTS

| | | | | |
|---|---|---|---|---|
| 5,753,808 | A | * | 5/1998 | Johnson ........................... 73/146 |
| 6,081,325 | A | * | 6/2000 | Leslie et al. ................ 356/237.2 |
| 6,151,100 | A | * | 11/2000 | Yamane et al. .................. 355/53 |
| 6,999,183 | B2 | * | 2/2006 | Nielsen et al. ................. 356/612 |
| 7,308,367 | B2 | | 12/2007 | Steele et al. |
| 7,784,107 | B2 | | 8/2010 | Kley |
| 8,619,235 | B2 | | 12/2013 | Van Drent |
| 2003/0053676 | A1 | * | 3/2003 | Shimoda et al. .............. 382/145 |
| 2003/0132401 | A1 | | 7/2003 | Yamada et al. |

(Continued)

FOREIGN PATENT DOCUMENTS

| | | |
|---|---|---|
| EP | 1457839 A2 | 9/2004 |
| JP | 2004-006509 A | 1/2004 |
| JP | 2008-215903 A | 9/2008 |

(Continued)

*Primary Examiner* — Sang Nguyen

(74) *Attorney, Agent, or Firm* — Suiter Swantz pc llo

(57) ABSTRACT

High speed height control of a surface of a substrate within a wafer inspection system includes positioning a substrate on a substrate stage of a dynamically adjustable substrate stage assembly, actuating the substrate perpendicular to the surface of the substrate, measuring a height error value of the surface of the substrate at a position of inspection of the surface, measuring a displacement value perpendicular to the surface of the substrate at the location of the substrate stage assembly, generating a displacement target from the height error value and the displacement value, and adjusting an actuation state of the actuator using the measured height error value and the generated displacement target in order to maintain the substrate surface at an imaging plane of a detector of the inspection system or a focus of illumination of the inspection system.

27 Claims, 7 Drawing Sheets

(56) References Cited

U.S. PATENT DOCUMENTS

2012/0015461 A1* 1/2012 Donaher et al. ............... 438/16
2014/0071457 A1 3/2014 Cai et al.

FOREIGN PATENT DOCUMENTS

| KR | 10-2005-005887 A | 1/2005 |
|---|---|---|
| KR | 10-2010-0062294 A | 6/2010 |

* cited by examiner

METHOD AND SYSTEM FOR HIGH SPEED HEIGHT CONTROL OF A SUBSTRATE SURFACE WITHIN A WAFER INSPECTION SYSTEM

CROSS-REFERENCE TO RELATED APPLICATION

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a regular (non-provisional) patent application of United States Provisional patent application entitled METHOD AND SYSTEM FOR HIGH SPEED HEIGHT CONTROL OF A SUBSTRATE SURFACE WITHIN A WAFER INSPECTION SYSTEM, naming Zhongping Cai and Jingyi Xiong as inventors, filed Aug. 23, 2013, Application Ser. No. 61/869,379.

FIELD OF THE INVENTION

The present invention generally relates to a system and method for height control of a substrate surface, and, in particular, a system and method for high speed height control of a substrate surface within a wafer inspection system.

BACKGROUND

As demand for ever-smaller semiconductor devices continues to increase, the demand for improved semiconductor wafer inspection processes continues to grow. One aspect of inspection tool operation includes increasing wafer height control speed for wafer scanning in order to reduce the height error at high scanning speed. For instance, height error may be used in a feedback control system so that wafer height follows a selected height target. A fundamental limit on the feedback control speed is the open loop resonance of the feedback control system. Therefore, it would be desirable to provide a system and method for increasing the control speed. Accordingly, the present invention seeks to cure the deficiencies of the prior art.

SUMMARY

A system for high speed height control of a surface of the substrate within a wafer inspection system is disclosed. In one aspect, the system includes, but is not limited to, a dynamically actuatable substrate stage assembly including a substrate stage for securing a substrate; an actuator configured to actuate the substrate along a direction substantially perpendicular to the surface of the substrate; a height error detection system configured to measure height error of a surface of the substrate at a position of inspection of the surface; and a displacement sensor operably coupled to the substrate stage assembly and configured to measure a displacement substantially perpendicular to the surface of the substrate at the location of the substrate stage assembly. Further, the system includes a feedback control system communicatively coupled to the height error detection system and the actuator, wherein the feedback control system is configured to: receive one or more height error measurements from the height error detection system; and responsive to the measured one or more height error measurements, adjust an actuation state of the actuator in order to maintain the substrate surface substantially at an imaging plane of a detector of the inspection system or a focus of illumination of the inspection system. In addition, a feed forward control system communicatively coupled to the height error detection system and the actuator, wherein the feed forward control system is configured to: receive one or more displacement measurements from the displacement sensor; responsive to one or more displacement values from the one or more displacement measurements with the one or more height error values from the one or more height error measurements, generate one or more displacement targets; and actuate the actuator using at least one of the one or more displacement targets in order to maintain the substrate surface substantially at an imaging plane of a detector of the inspection system or a focus of illumination of the inspection system.

A method for high speed height control of a surface of the substrate within a wafer inspection system is disclosed. In one aspect, the method includes, but is not limited to, positioning a substrate on a substrate stage of a dynamically adjustable substrate stage assembly; actuating the substrate along a direction substantially perpendicular to the surface of the substrate; measuring one or more height error values of the surface of the substrate at a position of inspection of the surface using a height error detection system; measuring one or more displacement values substantially perpendicular to the surface of the substrate at the location of the substrate stage assembly using a displacement sensor; generating one or more displacement targets from the one or more height error values and one or more displacement values; adjusting an actuation state of the actuator using the measured one or more height error values in order to maintain the substrate surface substantially at an imaging plane of a detector of the inspection system or a focus of illumination of the inspection system; and adjusting an actuation state of the actuator using the generated one or more displacement targets in order to maintain the substrate surface substantially at an imaging plane of a detector of the inspection system or a focus of illumination of the inspection system.

A system for high speed height control of a surface of the substrate within a wafer inspection system is disclosed. In one aspect, the system includes, but is not limited to, a dynamically actuatable substrate stage assembly including a substrate stage for securing a substrate; an actuator configured to actuate the substrate along a direction substantially perpendicular to the surface of the substrate; a height error detection system configured to measure height error of a surface of the substrate at a position of inspection of the surface; and a displacement sensor operably coupled to the substrate stage assembly and configured to measure a displacement substantially perpendicular to the surface of the substrate at the location of the substrate stage assembly. Further, the system includes a feedback control system communicatively coupled to the height error detection system and the actuator, wherein the feedback control system is configured to: receive one or more height error measurements from the height error detection system; and, responsive to the measured one or more height error measurements, adjust an actuation state of the actuator in order to maintain the substrate surface substantially at an imaging plane of a detector of the inspection system or a focus of illumination of the inspection system. In addition, a feed forward control system communicatively coupled to the height error detection system and the actuator, wherein the feed forward control system is configured to: receive one or more displacement measurements from the displacement sensor; responsive to one or more displacement values from the one or more displacement measurements with the one or more height error values from the one or more height error measurements, generate one or more displacement targets; and actuate the actuator using at least one of the one or more displacement targets in order to maintain the substrate surface substantially at an imaging plane of a detector of the inspection system or a focus of illumination of the inspection system. The system further comprising a track unit communicatively coupled to the feed forward system and configured to acquire a displacement target from one or more previous displacement target measurements, wherein the acquired displacement target is used as the feed forward target in order to reduce the effective phase delay of the feed forward control system.

A method for high speed height control of a surface of the substrate within a wafer inspection system is disclosed. In one aspect, the method includes, but is not limited to, positioning a substrate on a substrate stage of a dynamically adjustable substrate stage assembly; actuating the substrate along a direction substantially perpendicular to the surface of the substrate; measuring one or more height error values of the surface of the substrate at a position of inspection of the surface using a height error detection system; measuring one or more displacement values substantially perpendicular to the surface of the substrate at the location of the substrate stage assembly using a displacement sensor; generating one or more displacement targets from the one or more displacement targets of the one or more previous tracks; adjusting an actuation state of the actuator using the measured one or more height error values in order to maintain the substrate surface substantially at an imaging plane of a detector of the inspection system or a focus of illumination of the inspection system; and adjusting an actuation state of the actuator using the generated one or more displacement targets in order to maintain the substrate surface substantially at an imaging plane of a detector of the inspection system or a focus of illumination of the inspection system.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF THE DRAWINGS

The numerous advantages of the disclosure may be better understood by those skilled in the art by reference to the accompanying figures in which.

DETAILED DESCRIPTION OF THE INVENTION

Reference will now be made in detail to the subject matter disclosed, which is illustrated in the accompanying drawings.

Referring generally to FIGS. 1 through 7, a system and method for high speed height control of a surface of the substrate within a wafer inspection system is described, in accordance with the present disclosure. Embodiments of the present disclosure are directed to a system and method suitable for auto focusing in a substrate inspection system through the dynamic adjustment of height of an inspected substrate surface. In one embodiment, the dynamic adjustment of substrate height includes the measurement of substrate height error at selected regions of the substrate (e.g., regions of substrate inspection) coupled with feedback control of a substrate stage actuation device. In another embodiment, the dynamic adjustment of substrate height includes the measurement of one or more substrate stage displacement targets at selected regions of the substrate coupled with feed forward control of the substrate stage actuation device. In this regard, the measurement of the one or more displacement targets is realized through the combination of outputs from a displacement sensor and height error sensor. It is noted that the combination of displacement sensor and height error sensor outputs used in a feed forward control system allow a system to increase height control speed for substrate inspection scanning.

Figure 1:
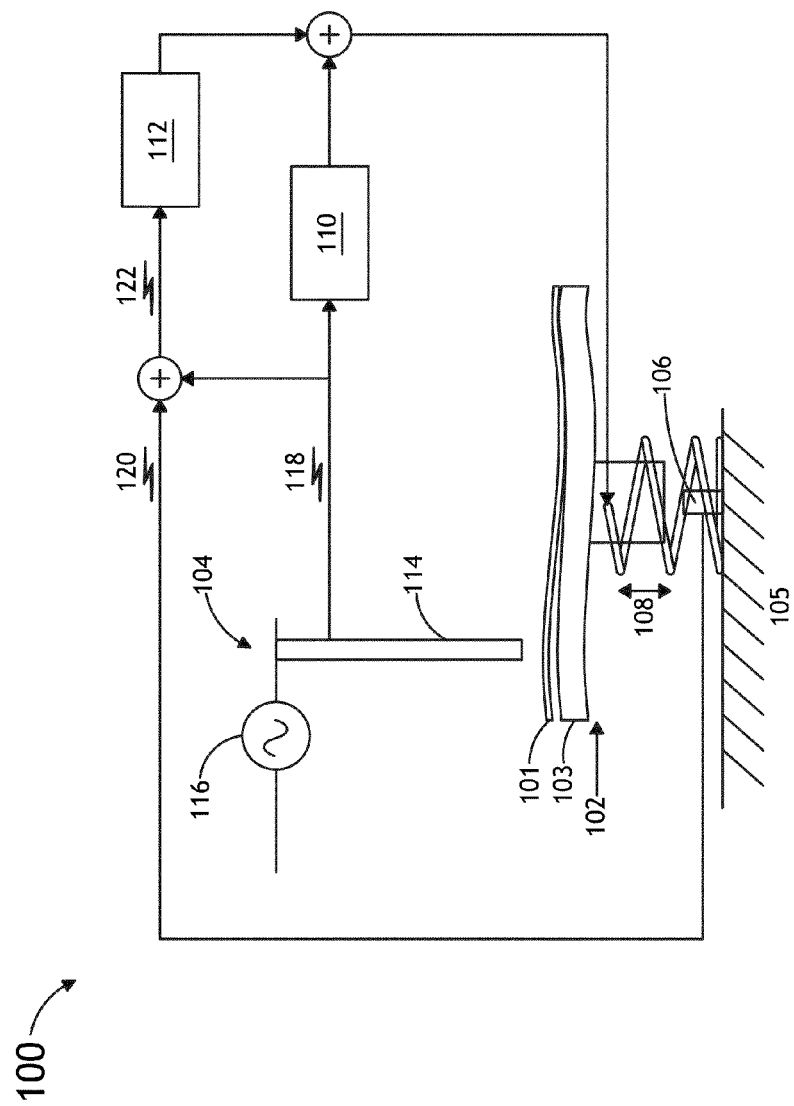
FIG. 1. illustrates a height control system having high speed height control loops of a surface of the substrate within a wafer inspection system, in accordance with the present disclosure.

FIG. 1 illustrates a system 100 for high speed height control of a surface of the substrate within a wafer inspection system in accordance with the present disclosure. In one embodiment, the system 100 for height control includes an actuatable substrate assembly 102. In another embodiment, the substrate assembly 102 includes a substrate stage 103 for securing a substrate 101. The substrate stage 103 may include any substrate stage architecture known in the art suitable for actuation along a direction generally normal to the surface of the substrate 101. For example, the substrate stage 103 may include a substrate chuck. In another embodiment, a chassis 105 is configured as a base frame for the substrate stage assembly 102.

In one embodiment, the substrate includes, but is not limited to, a semiconductor wafer. For the purpose of the present disclosure the terms "substrate" and "wafer" are utilized interchangeably. As used throughout the present disclosure, the term "substrate" generally refers to a wafer formed of a semiconductor material, such as, but not limited to, monocrystalline silicon, gallium arsenide, and indium phosphide. A wafer may include one or more layers. For example, such layers may include, but are not limited to, a resist, a dielectric material, a conductive material, or a semiconductive material. Many different types of such layers are known in the art, and the term "wafer" as used herein is intended to encompass a wafer of which all types of such layers may be formed. While the present disclosure focuses on the use of the present invention in the context of semiconductor wafer inspection and height control, it is noted herein that the present invention may be extended to any substrate type known in the art.

In one embodiment, the system 100 includes an actuator 108. In another embodiment, the actuator 108 is operably coupled to the substrate stage assembly 102. In another embodiment, the actuator 108 is configured to actuate the substrate 101 along a direction substantially perpendicular to the surface of the substrate 101 at the location of the substrate stage assembly 102. For example, the actuator 108 may be mechanically coupled the substrate stage assembly 102. In this regard, the actuator 108 may adjust the substrate 101 by actuating the substrate stage 103. The actuator 108 may include any actuator known to be suitable for actuating a substrate along a selected direction (e.g., vertical direction). For example, the actuator 108 may include, but is not limited to, a voice coil actuator.

In one embodiment, the system 100 includes a height error detection system 104 configured to measure height error of a surface of the substrate 101 at a position of inspection on the surface. In another embodiment, the height error detection system 104 includes one or more optical sensors 114 configured to detect height error values 118 on the surface of the substrate 101 at a position of inspection on the surface of the substrate 101. The one or more optical sensors 114 for use in the height error detection system 104 may include any optical sensor suitable for height error detection known in the art. For example, the one or more height error detection optical sensors 114 may include, but are not limited to, one or more bi-cell detectors, one or more quad-cell detectors, one or more line CCD detectors, one or more line CMOS detectors or the like. Optical configurations suitable for implementation in the height error detection system 114 are described in greater detail further herein.

In one embodiment, the height error detection system 104 receives a height target 116 for the surface of the substrate 101. In another embodiment, the height target source (controller) is communicatively coupled with the height error sensor 114 for generating height error signal 118. For example, the height error signal 118 may be generated by subtracting the measured height of the surface of the substrate 101 from the preset height target 116.

In one embodiment, the system 100 includes a displacement sensor 106. In another embodiment, the displacement sensor 106 is operably coupled to the substrate stage assembly 102. For example, the displacement sensor 106 may be mechanically coupled with the substrate stage assembly 102. In another embodiment, the displacement sensor 106 measures one or more displacement values 120 from one or more displacement measurements. It is noted herein that the measured one or more displacement values 120 are substantially perpendicular to the surface of the substrate 101 at the location of the substrate assembly 102. In another embodiment, the displacement sensor 106 is a Z-stage displacement sensor. The displacement sensor 106 may include any sensor suitable for measuring displacement of the stage assembly 102. For example the displacement sensor may include, but is not limited to, an Eddy current sensor. By way of another example, the displacement sensor 106 may include, but is not limited to, an optical sensor.

In one embodiment, the system 100 includes a feedback control system 110. In another embodiment, the feedback control system 110 is communicatively coupled to the height error detection system 104. In another embodiment, the feedback control system 110 is communicatively coupled to the actuator 108. In another embodiment, the feedback control system 110 receives one or more height error values 118 from one or more height error measurements using the height error detection system 104.

In one embodiment, the feedback control system 110 is responsive to the measured one or more height error values 118. In another embodiment, the feedback system 110 adjusts an actuation state of the actuator 108 in order to maintain the surface of the substrate 101 substantially at an imaging plane of a detector of the inspection system 100. In another embodiment, the feedback system 110 adjusts an actuation state of the actuator 108 in order to maintain a focus of illumination of the inspection system 100.

In one embodiment, the system 100 includes a feed forward control system 112. In another embodiment, the feed forward control system 112 is communicatively coupled to the height error detection system 104. In another embodiment, the feed forward control system 112 is communicatively coupled to the actuator 108. In another embodiment, the feed forward control system 112 receives one or more displacement measurement values 120 from the one or more displacement measurements using the displacement sensor 106.

In another embodiment, the feed forward control system 112 is responsive to the measured one or more displacement measurement values 120 from the one or more displacement measurements with the one or more height error values 118 from the one or more height error measurements to generate one or more displacement targets 122. For example, the one or more displacement targets 122 may be generated by adding the one or more height error values 118 to the one or more displacement values 120.

In another embodiment, the feed forward control system 112 actuates the actuator 108 using at least one of the one or more displacement targets 122 in order to maintain the surface of the substrate 101 substantially at an imaging plane of a detector of the inspection system 100. In another embodiment, the feed forward control system 112 actuates the actuator 108 using at least one of the one or more displacement targets 122 in order to maintain a focus of illumination of the inspection system.

FIG. 2 illustrates an example operation of high speed height control carried out by a system consistent with system 100, in accordance with the present disclosure. The feedback height control bandwidth for the height control loop is 200 Hz, for the data of FIG. 2.

Figure 2A:
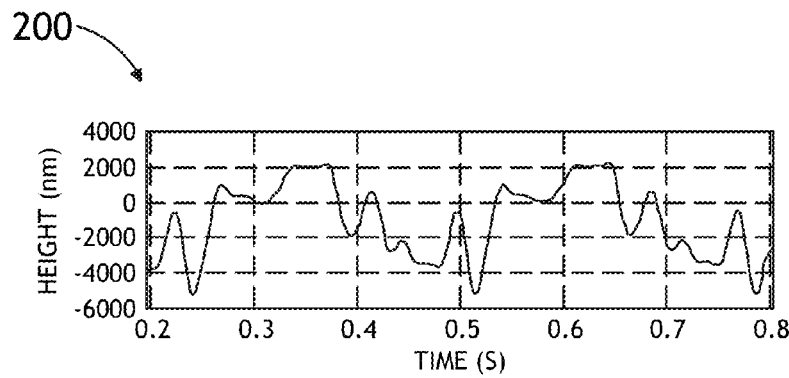
FIGS. 2A-2C illustrate an example operation of high speed height control carried out by the height control system having high speed height control loops of a surface of the substrate within a wafer inspection system, in accordance with the present disclosure.
Figure 2B:
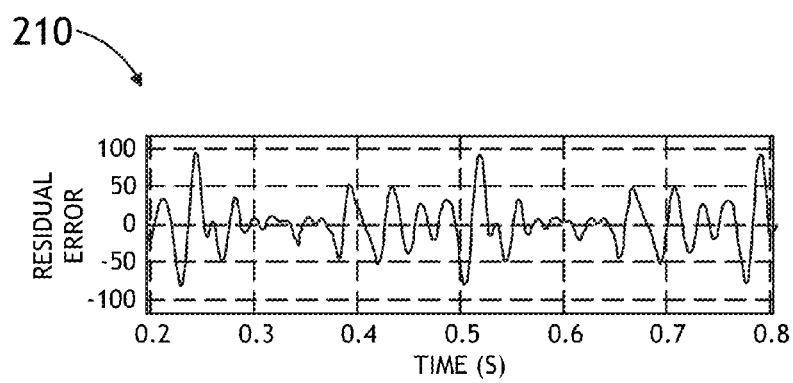
Figure 2C:
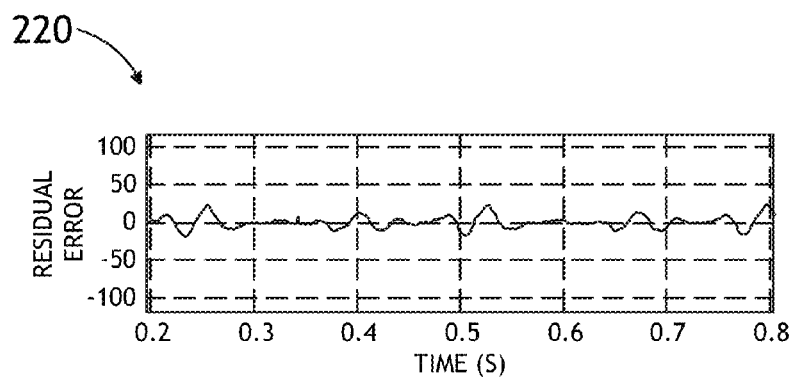

FIG. 2A depicts a height runout of the substrate 101. The height runout is approximately 8,000 nm peak-to-peak with the shown substrate motion speed. After 200 Hz bandwidth height control by the feedback control system 110, the residual height error 118 is approximately 175 nm peak-to-peak, as shown in FIG. 2B. FIG. 2C depicts a further reduced residual height error 118 of the substrate 101 runout by adding a feed forward control system 112 to control the actuator 106. In this aspect, the feed forward control system 112 increases the control speed. The residual height error 118 in FIG. 2C is approximately 45 nm peak-to-peak in this example.

Figure 3:
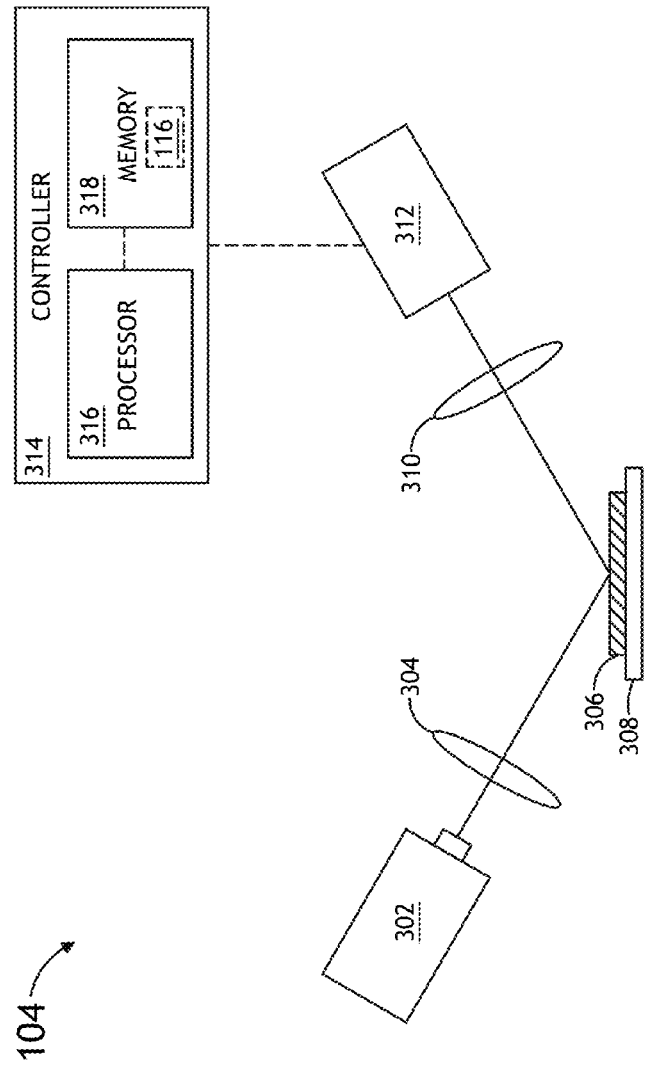
FIG. 3 illustrates a height error detection system, in accordance with the present disclosure.

FIG. 3 illustrates a height error detection system 104 of the system 100, in accordance with the present disclosure. In one embodiment, the height error detection system 104 includes a substrate stage 308. In another embodiment, the substrate stage 308 is configured to dispose the substrate 306. The substrate stage 308 includes any appropriate mechanical assembly known in the art. For example, the substrate stage 103 may include, but is not limited to, a substrate chuck.

In another embodiment, the height error detection system 104 includes one or more light sources 302 configured to generate a light beam of a selected wavelength or wavelength range. In another embodiment, the one or more light sources 302 include any narrowband light sources known in the art. For example, the one or more light sources 302 may include, but are not limited to, one or more lasers (e.g., one or more infrared lasers) or one or more narrowband LEDs. By way of another example, the one or more light sources may include, but are not limited to, any broadband light source. For example, the one or more light sources 302 may include a collimated and/or filtered broadband source. By way of another example, the one or more light sources 302 may include, but are not limited to, a broadband spectrum LED (e.g., WLED with phosphor layer). By way of another example, the one or more light sources 302 may include, but are not limited to, a superluminescent LED (SLED). In another embodiment, the one or more light sources 302 are configured to direct a light beam to a portion of the surface of the substrate 306 through the one or more focusing lenses 304. In turn, the one or more focusing lenses 304 are configured to direct light from the one or more light sources 302 to at least a portion of the surface of the substrate 306.

In another embodiment, the height error detection system 104 includes one or more sensors 312. In another embodiment, the one or more sensors 312 are configured to monitor one or more characteristics of light reflected from the surface of the substrate 306. For example, the one or more sensors 312 may measure, but are not limited to, one or more height error values 118 of the surface of the substrate 306. In another embodiment, the light beam reflected by a portion of the substrate 306 is collected by a lens collector 310, focused and directed to the sensor 312. The one or more sensors 312 of the height error detection system 104 may include any appropriate sensors known in the art capable of detecting a light beam generated by the one or more light sources 302. For example, the one or more sensors 312 may include, but are not limited to, one or more bi-cell detectors, one or more quad-cell detectors, one or more line CCD detectors, one or more line CMOS detectors or the like. Upon receiving a reflection beam from the surface of the substrate 304, the one or more sensors 312 convert the received light into one or more height error values 118.

It is further recognized herein that the height error detection system 104 may include any number of additional optic elements to carry out the described embodiments. For example, the height error detection system 104 may further include, but is not limited to, a set of optic components suitable for directing and/or focusing light beams from the one or more light sources 302 onto the surface of the substrate 306. By way of another example, the height error detection system 104 may include, but is not limited to, a set of optic components for collecting and/or reflecting a light beam from the surface of the substrate 306 onto a portion of the one or more sensors 312.

In one embodiment, the height error detection system 104 includes a controller 314 configured to measure the height error values of the substrate 306. In another embodiment, the controller 314 is communicatively coupled to the one or more sensors 312 of the height error detection system 104. For example, the controller 314 may be communicatively coupled to the output of the one or more sensors 312 of the height error detection system 104. Further, the controller 314 may be coupled to the one or more sensors 312 in any suitable manner such that the controller 314 can receive the output acquired by the height error detection system 104. For example, the controller 314 may be coupled via a wireline or wireless connection.

In one embodiment, the controller 314 is configured to receive the one or more monitored light characteristics from the one or more sensors 312. For example, the controller 314 may receive one or more signals indicative of the measured one or more height error values 118 of the surface of the substrate 306. In this regard, the one or more sensors 312 may transmit the measured height error values as a function of time.

In one embodiment, the controller 314 includes one or more processors 316 and one or more memory 318. In another embodiment, the one or more memory 318 of the controller 314 contains a set of program instructions configured to cause the one or more processors 316 of the controller 314 to carry out the height error measurements described throughout the present disclosure.

In another embodiment, the one or more memory 318 contains a height target 116 configured to generate one or more height error values 118. For example, the controller 314 may measure the one or more height values of the surface of the substrate 306. In this regard, the measured one or more height values may subtract from the stored height target 116 to generate one or more height error values 118. In another embodiment, the generated one or more height error values are also stored in the one or more memory 318.

Figure 4:
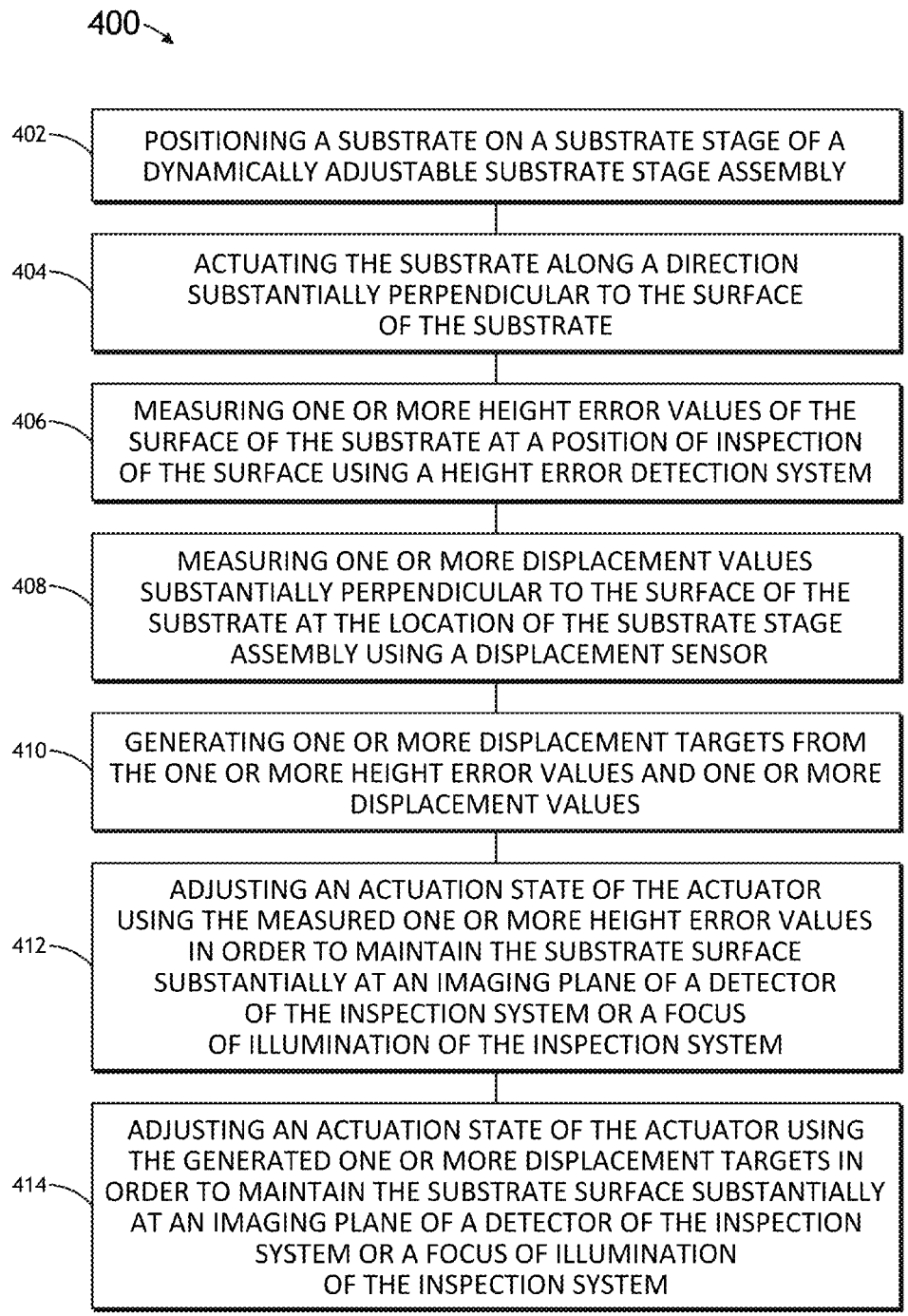
FIG. 4 illustrates a method for high speed height control of a surface of the substrate within a wafer inspection system, in accordance with the present disclosure.

FIG. 4 illustrates a method 400 for high speed height control of a surface of the substrate within a wafer inspection system 100, in accordance with the present disclosure. It is noted herein that method 400 of the present disclosure may be carried out utilizing one or more of the systems or sub-systems described previously herein, however, the various structural elements and configurations described previously herein should not be interpreted as limitations on method 400 as it is anticipated that other structures and configurations may be used to carry out method 400.

In step 402, a substrate 101 is positioned on substrate stage 103 of a dynamically adjustable substrate stage assembly 102. In step 404, the substrate 101 is actuated along a direction substantially perpendicular to the surface of the substrate 101. In step 406, one or more height error values 118 of the surface of the substrate 101 are measured at a position of inspection of the surface using a height error detection system 104. In step 408, one or more displacement values 120 substantially perpendicular to the surface of the substrate 101 are measured at the position of the substrate stage assembly 102 using a displacement sensor 106. In step 410, one or more displacement targets 122 are generated from the measured one or more height error values 118 and the one or more displacement values 120. In step 412, an actuation state of the actuator 108 is adjusted using the measured one or more height error values 118 in order to maintain the substrate surface substantially at an imaging plane of a detector of the inspection system 100 or a focus of illumination of the inspection system. In step 414, an actuation state of the actuator 108 is adjusted using the generated one or more displacement targets 122 in order to maintain the substrate surface substantially at an imaging plane of a detector of the inspection system 100 or a focus of illumination of the inspection system. It is noted further herein that the order of the steps of method 400 is not limiting as it is recognized that the inspection and height adjustment processes can be carried out in any order or simultaneously.

Figure 5:
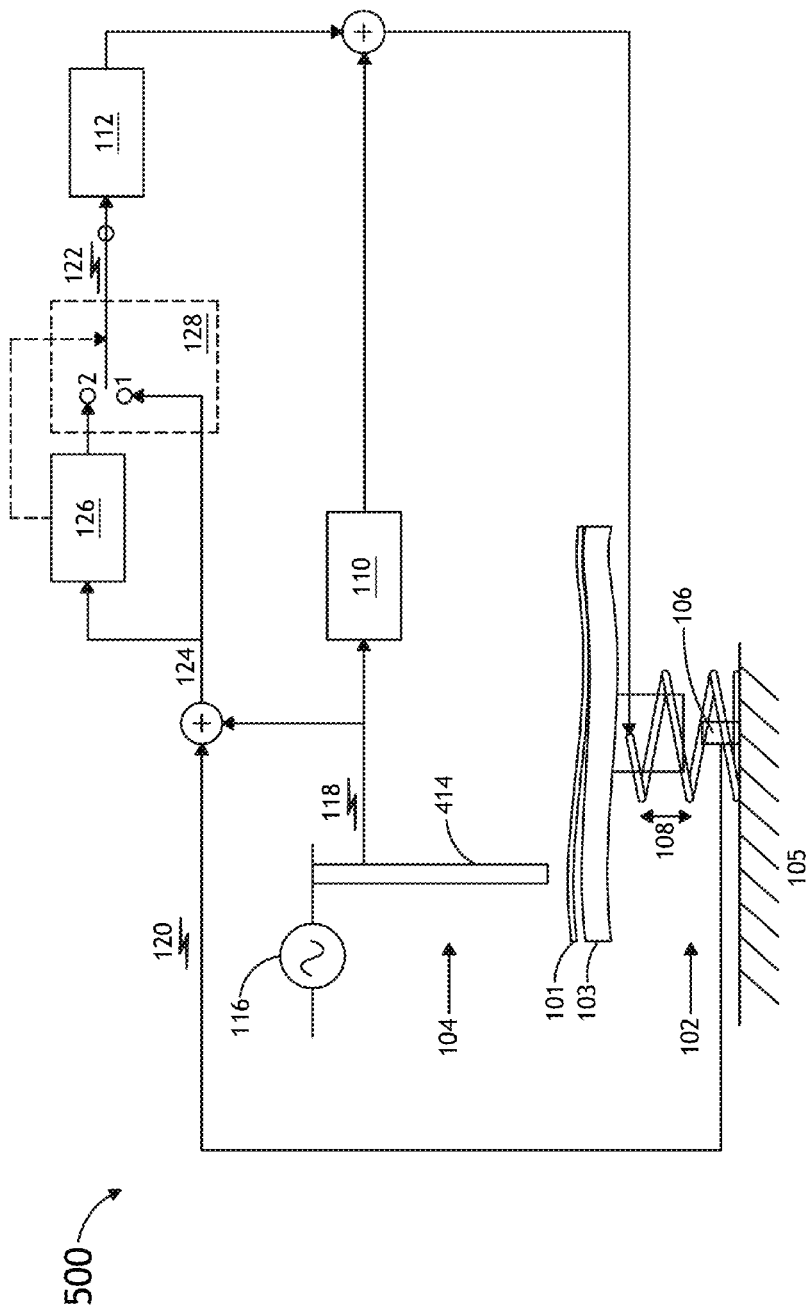
FIG. 5 illustrates a high speed height control system of a surface of the substrate within a wafer inspection system, in accordance with the present disclosure.

FIG. 5 illustrates another embodiment of the system for high speed height control of a surface of the substrate within a wafer inspection system, in accordance with the present disclosure. It is noted herein that the components and embodiments described in FIG. 1 are extendable to system 500, unless otherwise noted.

In one embodiment, the system 500 includes a data switch 128. In another embodiment, the data switch 128 contains two and more ports. In another embodiment, at least one port of the data switch 128 is communicatively coupled to the feed forward control system 112. For example, as shown in FIG. 5, the data switch 128 may be communicatively coupled to the feed forward control system 112 through pathway 1. By way of another example, the data switch 128 may be communicatively coupled to the feed forward control system 112 through pathway 2.

In one embodiment, the system 500 includes a track unit 126. In another embodiment, the track unit 126 is configured to acquire and maintain one or more displacement targets 124 generated from the one or more height error values 118 and the one or more displacement values 120. In another embodiment, the track unit 126 is communicatively coupled to the feed forward control system 112 through one or more ports of the data switch 128. For example, the track unit 126 may be communicatively coupled to the feed forward control system 112 through pathway 2 of the data switch 128. In another embodiment, the track unit 126 uses the acquired one or more displacement targets 124 from one or more previous tracks as one or more displacement targets 122 for a current track. Further, the one or more displacement targets 122 of the current track may be sent to the feed forward control system 112. For example, when the one or more displacement targets 124 has been acquired after one or more first scanning routines, the switch 128 may shift from pathway 1 to pathway 2 in order to utilize the one or more displacement targets 124 of the one or more previous tracks as the one or more displacement targets 122 for the current track. It is noted herein that the one or more displacement targets 122 of the current track along a given substrate inspection path are nearly the same as the one or more displacement targets 124 of the one or more previous tracks mentioned throughout the present disclosure. In this regard, the one or more displacement targets 124 of the one or more previous tracks can predict the one or more displacement targets 122 of the current track precisely, and reduce effective phase delay of the feed forward control system 112.

In one embodiment, the track unit 126 uses a single acquired displacement target 124 of the previous track to predict the displacement target 122 of the current track. In another embodiment, the track unit 126 acquires two or more displacement targets 124 of two or more previous tracks to predict the displacement target 122 of the current track for the feed forward control 112. For example, the acquired two or more displacements targets 124 of the two or more the previous tracks may be averaged in order to predict the displacement target 122 of the current track for the feed forward control system 112.

In one embodiment, the track unit 126 of the system 500 includes one or more processors configured to acquire the one or more displacement targets. In another embodiment, the track unit 126 of the system 500 includes one or more memory configured to maintain the one or more displacement targets. In another embodiment, the one or more memory is configured to maintain a set of program instructions to cause the one or more processors to acquire one or more displacement targets of the one or more previous tracks. In another embodiment, a set of program instructions are configured to send the acquired one or more displacement targets to the feed forward control system 112 in order to control the actuator.

Figure 6:
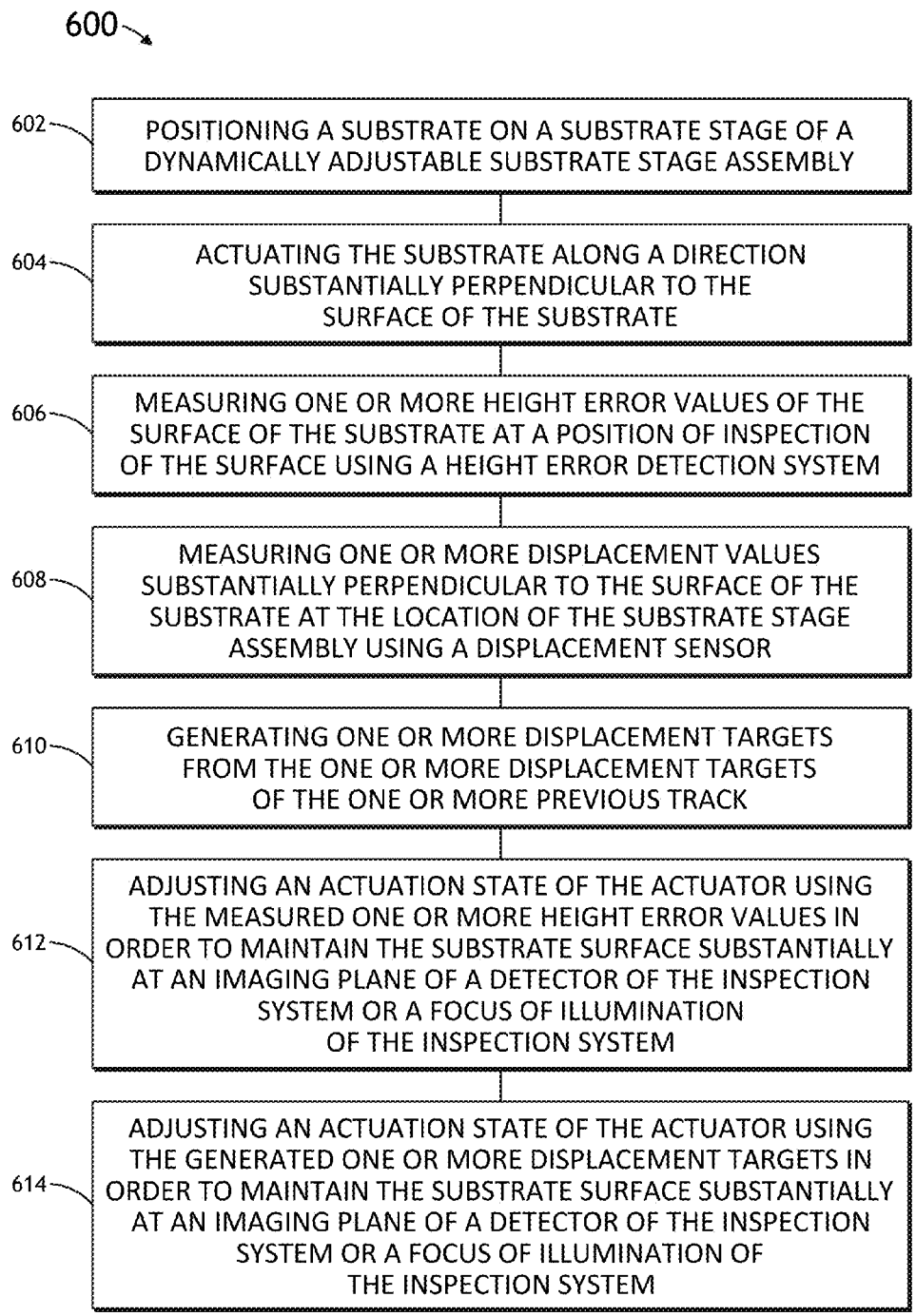
FIG. 6 illustrates a method for high speed height control of a surface of the substrate within a wafer inspection system, in accordance with the present disclosure.

FIG. 6 illustrates a method 600 for high speed height control of a surface of the substrate within a wafer inspection system 500, in accordance with the present disclosure. It is noted herein that method 600 of the present disclosure may be carried out utilizing one or more of the systems or sub-systems described previous herein, however, the various structural elements and configurations described previously herein should not be interpreted as limitations on method 600 as it is anticipated that other structures and configurations may be used to carry out method 600.

In step 602, a substrate 101 is positioned on substrate stage 103 of a dynamically adjustable substrate stage assembly 102. In step 604, the substrate 101 is actuated along a direction substantially perpendicular to the surface of the substrate 101. In step 606, one or more height error values 118 of the surface of the substrate 101 are measured at a position of inspection of the surface using a height error detection system 104. In step 608, one or more displacement values 120 substantially perpendicular to the surface of the substrate 101 are measured at the position of the substrate stage assembly 102 using a displacement sensor 106. In step 610, one or more displacement targets 122 are generated from the one or more displacement targets of the one or more previous tracks 124. In step 612, an actuation state of the actuator 108 is adjusted using the measured one or more height error values 118 in order to maintain the substrate surface substantially at an imaging plane of a detector of the inspection system 100 or a focus of illumination of the inspection system. In step 614, an actuation state of the actuator 108 is adjusted using the generated one or more displacement targets 122 in order to maintain the substrate surface substantially at an imaging plane of a detector of the inspection system 100 or a focus of illumination of the inspection system. It is noted further herein that the order of the steps of method 600 is not limiting as it is recognized that the inspection and height adjustment processes can be carried out in any order or simultaneously.

Figure 7:
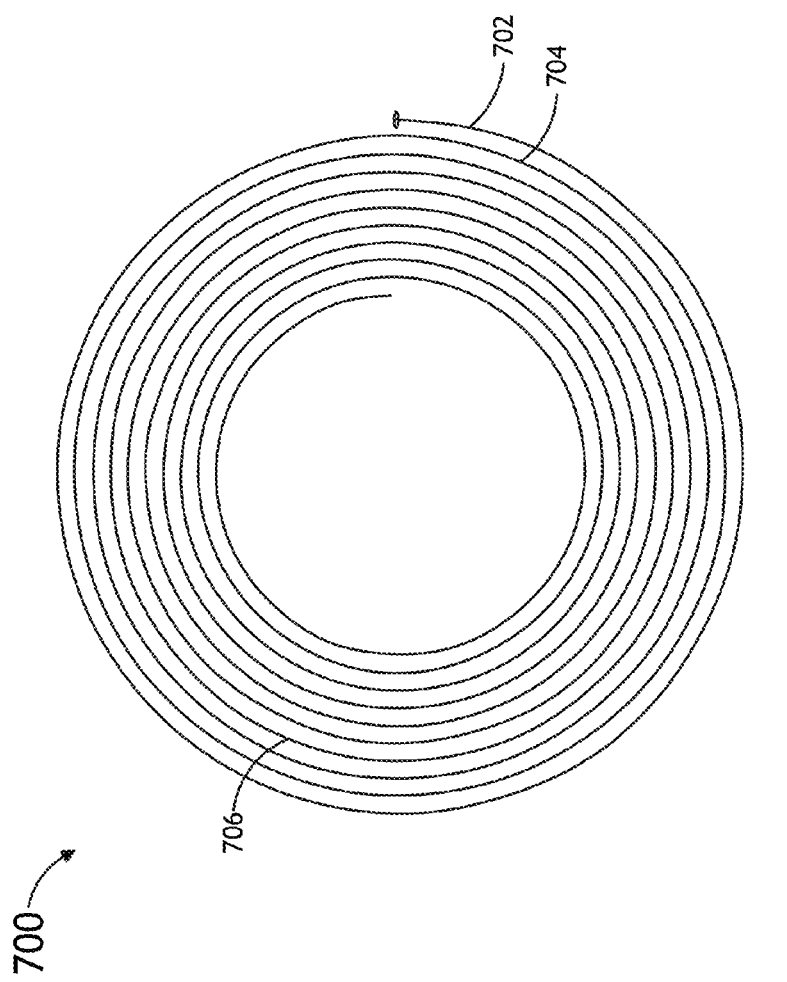
FIG. 7 illustrates a top view of a two-dimensional substrate sequential scanning pattern, in accordance with one embodiment of the system of the present invention.

FIG. 7 illustrates a top view of a two-dimensional substrate sequential scanning pattern, in accordance with one embodiment of the system 500 of the present invention. In one embodiment, the scanning of the substrate 101 includes a two-dimensional variable radius/variable angle scanning. For example, the scanning of the substrate 101 may include a two-dimensional scanning pattern 700 that forms any scanning pattern known in the art.

For instance, as shown in FIG. 7, the two-dimensional scanning pattern 700 may include a spiral pattern. In one embodiment, the spiral pattern 700 is scanned from the center of a wafer to the edge of the wafer, or, alternatively, from the edge of the wafer to the center of the wafer. In another embodiment, the displacement target along a current track 702 is very near to the displacement target along the previous track 704. In another embodiment, the displacement target of previous track 704 is used to predict the current track 706. In another embodiment, two or more displacement targets along previous tracks 704 and 706 are acquired and used to generate the displacement target of current track 702. For example, two or more displacement targets along previous tracks 704 and 706 are acquired and averaged to be used as the displacement target of current track 702.

Those skilled in the art will recognize that the state of the art to the described systems and methods in the fashion set forth herein, and thereafter, use engineering practices to integrate such described systems and methods into high speed wafer inspections systems. That is, at least a portion of the systems and methods described herein can be integrated into a high speed wafer inspection system via a reasonable amount of experimentation. A typical high speed wafer inspection system may be implemented utilizing any suitable commercially available components, such as those typically found in wafer inspection and/or auto focusing systems.

In some embodiments, various steps, functions, and/or operations of the systems described herein (and the following methods) are carried out by one or more of the following: electronic circuits, logic gates, multiplexers, programmable logic devices, ASICs, analog or digital controls/switches, microcontrollers, or computing systems. The controller may include, but is not limited to, a personal computing system, mainframe computing system, workstation, image computer, parallel processor, or any other device known in the art. In general, the term "computing system" is broadly defined to encompass any device having one or more processors, which execute instructions from a carrier medium, or memory. The program instructions implementing methods such as those described herein may be transmitted over or stored on carrier medium. The carrier medium may include a storage medium such as a read-only memory, a random access memory, a magnetic or optical disk, a non-volatile memory, a solid state memory, a magnetic tape and the like. A carrier medium may include a transmission medium such as a wire, cable, or wireless transmission link.

It should be recognized that the various steps described throughout the present disclosure may be carried out by a single controller (or computer system) or, alternatively, multiple controllers (or multiple computer systems). Moreover, different sub-systems of the system may include one or more computing or logic system suitable for carrying out at least a portion of the steps described above. Therefore, the above description should not be interpreted as a limitation on the present invention but merely an illustration. Further, the controller may be configured to perform any other step(s) of any of the method embodiments described herein.

Those having skill in the art will appreciate that there are various vehicles by which processes and/or systems and/or other technologies described herein can be carried out (e.g., hardware, software, and/or firmware), and that the preferred vehicle will vary with the context in which the processes and/or systems and/or other technologies are deployed.

All of the methods described herein may include storing results of one or more steps of the method embodiments in a storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. Furthermore, the results may be stored "permanently," "semi-permanently," temporarily, or for some period of time. For example, the storage medium may be random access memory (RAM), and the results may not necessarily persist indefinitely in the storage medium.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto.

What is claimed:

1. A system for high speed height control of a surface of the substrate within a wafer inspection system comprising:
    a dynamically actuatable substrate stage assembly including a substrate stage for securing a substrate;
    an actuator configured to actuate the substrate along a direction substantially perpendicular to the surface of the substrate;
    a height error detection system configured to measure height error of a surface of the substrate at a position of inspection of the surface;
    a displacement sensor operably coupled to the substrate stage assembly and configured to measure a displacement substantially perpendicular to the surface of the substrate at the location of the substrate stage assembly;
    a feedback control system communicatively coupled to the height error detection system and the actuator, wherein the feedback control system is configured to:
        receive one or more height error measurements from the height error detection system; and
        responsive to the measured one or more height error measurements, adjust an actuation state of the actuator in order to maintain the substrate surface substantially at an imaging plane of a detector of the inspection system or a focus of illumination of the inspection system; and
    a feed forward control system communicatively coupled to the height error detection system and the actuator, wherein the feed forward control system is configured to:
        receive one or more displacement measurements from the displacement sensor;
        responsive to one or more displacement values from the one or more displacements measurements with the one or more height error values from the one or more height error measurements, generate one or more displacement targets; and
        actuate the actuator using at least one of the one or more displacement targets in order to maintain the substrate surface substantially at an imaging plane of a detector of the inspection system or a focus of illumination of the inspection system.

2. The system of claim 1, wherein the substrate comprises: a semiconductor wafer.

3. The system of claim 1, wherein the substrate stage assembly comprises:
    a substrate stage platform; and
    a substrate chuck configured to secure the substrate.

4. The system of claim 1, wherein the height error detection system comprises:
    a light source configured to generate a light beam;
    an optical sub-system configured to direct the light beam onto the surface of the substrate at substantially the position of inspection of the inspection system; and a height error sensor configured to detect a position of the light beam reflected from the surface of the substrate, wherein a height error controller is configured to determine a height error value of the surface of the substrate based on the measured position of the light beam at the sensor and a height target.

5. The system of claim 4, wherein the light source comprises:
at least one of a narrowband light source and a broadband light source.

6. The system of claim 4, wherein the height error sensor comprises:
one or more optical bicell sensors.

7. The system of claim 4, wherein the height error controller comprises:
one or more processors; and
one or more memory for storing the height target of a position of the light beam reflected from the surface of the substrate and a set of program instructions, the program instructions configured to determine a height error value of the surface of the substrate based on the measured position of the light beam at the sensor and a height target.

8. The system of claim 1, wherein the actuator further comprises:
a voice coil driven actuator.

9. The system of claim 1, wherein the displacement sensor further comprises:
one or more Eddy current sensors.

10. The system of claim 1, wherein the feedback control system configured to adjust an actuation state of the actuator is further configured to:
adjust an actuation state of the actuator in order to control the at least one of the one or more height errors of the substrate surface at the position of inspection.

11. The system of claim 1, wherein the feed forward control system configured to combine the one or more displacements with the one or more height errors to generate one or more displacement targets is further configured to:
add the one or more displacements with the one or more height errors to generate one or more displacement targets.

12. The system of claim 1, wherein the inspection system comprises:
at least one of a brightfield inspection system and a darkfield inspection system.

13. A method for high speed height control of a surface of the substrate within a wafer inspection system comprising:
positioning a substrate on a substrate stage of a dynamically adjustable substrate stage assembly;
actuating the substrate along a direction substantially perpendicular to the surface of the substrate;
measuring one or more height error values of the surface of the substrate at a position of inspection of the surface using a height error detection system;
measuring one or more displacement values substantially perpendicular to the surface of the substrate at the location of the substrate stage assembly using a displacement sensor;
generating one or more displacement targets from the one or more height error values and one or more displacement values;
adjusting an actuation state of the actuator using the measured one or more height error values in order to maintain the substrate surface substantially at an imaging plane of a detector of the inspection system or a focus of illumination of the inspection system; and
adjusting an actuation state of the actuator using the generated one or more displacement targets in order to maintain the substrate surface substantially at an imaging plane of a detector of the inspection system or a focus of illumination of the inspection system.

14. A system for high speed height control of a surface of the substrate within a wafer inspection system comprising:
a dynamically actuatable substrate stage assembly including a substrate stage for securing a substrate;
an actuator configured to actuate the substrate along a direction substantially perpendicular to the surface of the substrate;
a height error detection system configured to measure height error of a surface of the substrate at a position of inspection of the surface;
a displacement sensor operably coupled to the substrate stage assembly and configured to measure a displacement substantially perpendicular to the surface of the substrate at the location of the substrate stage assembly;
a feedback control system communicatively coupled to the height error detection system and the actuator, wherein the feedback control system is configured to:
receive one or more height error measurements from the height error detection system; and
responsive to the measured one or more height error measurements, adjust an actuation state of the actuator in order to maintain the substrate surface substantially at an imaging plane of a detector of the inspection system or a focus of illumination of the inspection system;
a feed forward control system communicatively coupled to the height error detection system and the actuator, wherein the feed forward control system is configured to:
receive one or more displacement measurements from the displacement sensor;
responsive to one or more displacement values from the one or more displacements measurements with the one or more height error values from the one or more height error measurements, generate one or more displacement targets; and
actuate the actuator using at least one of the one or more displacement targets in order to maintain the substrate surface substantially at an imaging plane of a detector of the inspection system or a focus of illumination of the inspection system; and
a track unit communicatively coupled to the feed forward system and configured to acquire a displacement target from one or more previous displacement target measurements, wherein the acquired displacement target is used as the feed forward target in order to reduce an effective phase delay of the feed forward control system.

15. The system of claim 14, wherein the substrate comprises:
a semiconductor wafer.

16. The system of claim 14, wherein the substrate stage assembly comprises:
a substrate stage platform; and
a substrate chuck configured to secure the substrate.

17. The system of claim 14, wherein the height error detection system comprises:
a light source configured to generate a light beam;
an optical sub-system configured to direct the light beam onto the surface of the substrate at substantially the position of inspection of the inspection system; and
a height error sensor configured to detect a position of the light beam reflected from the surface of the substrate, wherein a height error controller is configured to determine a height error value of the surface of the substrate based on the measured position of the light beam at the sensor and a height target.

18. The system of claim 17, wherein the light source comprises:
   at least one of a narrowband light source and a broadband light source.

19. The system of claim 17, wherein the height error sensor comprises:
   one or more optical bicell sensors.

20. The system of claim 17, wherein the height error controller comprises:
   one or more processors; and
   one or more memory for storing the height target of a position of the light beam reflected from the surface of the substrate and a set of program instructions, wherein the program instructions are configured to determine a height error value of the surface of the substrate based on the measured position of the light beam at the sensor and a height target.

21. The system of claim 14, wherein the actuator further comprises:
   a voice coil driven actuator.

22. The system of claim 14, wherein the Z stage displacement sensor further comprises:
   one or more Eddy current sensors.

23. The system of claim 14, wherein the track unit comprises:
   one or more processors; and
   one or more memory for maintaining a set of program instructions, wherein the program instructions are configured to cause the one or more processors to:
      acquire one or more previous displacement targets, the acquired one or more previous displacement targets being stored in the one or more memory; and
      feed forward the acquired one or more previous displacement targets to control the actuator in order to reduce the effective phase delay of the feed forward.

24. The system of claim 14, wherein the feedback control system configured to adjust an actuation state of the actuator is further configured to:
   adjust an actuation state of the actuator in order to control the at least one of the one or more height errors of the substrate surface at the position of inspection.

25. The system of claim 14, wherein the feed forward control system configured to combine the one or more displacements with the one or more height errors to generate one or more displacement targets is further configured to:
   add the one or more displacements with the one or more height errors to generate one or more displacement targets.

26. The system of claim 14, wherein the inspection system comprises:
   at least one of a brightfield inspection system and a darkfield inspection system.

27. A method for high speed height control of a surface of the substrate within a wafer inspection system comprising:
   positioning a substrate on a substrate stage of a dynamically adjustable substrate stage assembly;
   actuating the substrate along a direction substantially perpendicular to the surface of the substrate;
   measuring one or more height error values of the surface of the substrate at a position of inspection of the surface using a height error detection system;
   measuring one or more displacement values substantially perpendicular to the surface of the substrate at the location of the substrate stage assembly using a displacement sensor;
   generating one or more displacement targets from the one or more displacement targets of the one or more previous tracks;
   adjusting an actuation state of the actuator using the measured one or more height error values in order to maintain the substrate surface substantially at an imaging plane of a detector of the inspection system or a focus of illumination of the inspection system; and
   adjusting an actuation state of the actuator using the generated one or more displacement targets in order to maintain the substrate surface substantially at an imaging plane of a detector of the inspection system or a focus of illumination of the inspection system.

* * * * *